(12) United States Patent
Choi et al.

(10) Patent No.: US 9,421,069 B2
(45) Date of Patent: Aug. 23, 2016

(54) SURGICAL GRASPER FOR MEASURING FORCE

(71) Applicant: Research & Business Foundation SUNGKYUNKWAN UNIVERSITY, Suwon-si (KR)

(72) Inventors: Hyouk Ryeol Choi, Gunpo-si (KR); Dong Hyuk Lee, Cheongju-si (KR); Ui Kyum Kim, Anseong-si (KR)

(73) Assignee: RESEARCH & BUSINESS FOUNDATION SUNGKYUNKWAN UNIVERSITY, Suwon-si (KR)

(*) Notice: Subject to any disclaimer, the term of this patent is extended or adjusted under 35 U.S.C. 154(b) by 10 days.

(21) Appl. No.: 14/591,380

(22) Filed: Jan. 7, 2015

(65) Prior Publication Data

US 2015/0190203 A1    Jul. 9, 2015

(30) Foreign Application Priority Data

Jan. 7, 2014    (KR) .................. 10-2014-0001947

(51) Int. Cl.
*A61B 5/00* (2006.01)
*A61B 19/00* (2006.01)
*A61B 17/29* (2006.01)
*A61B 17/28* (2006.01)

(52) U.S. Cl.
CPC .............. *A61B 19/46* (2013.01); *A61B 5/0053* (2013.01); *A61B 5/4836* (2013.01); *A61B 17/29* (2013.01); *A61B 90/06* (2016.02); *A61B 34/30* (2016.02); *A61B 2017/2825* (2013.01); *A61B 2017/2926* (2013.01); *A61B 2090/065* (2016.02); *A61B 2505/05* (2013.01); *A61B 2562/0247* (2013.01)

(58) Field of Classification Search
CPC .............. A61B 17/29; A61B 17/00234; A61B 2017/2926; A61B 18/1445; A61B 2018/1455; A61B 5/0053; A61B 5/4836; A61B 19/46
See application file for complete search history.

(56) References Cited

U.S. PATENT DOCUMENTS

| | | | |
|---|---|---|---|
| 9,107,648 B2* | 8/2015 | Ransden ............ | A61B 17/0401 |
| 9,186,204 B2* | 11/2015 | Nishimura ......... | A61B 18/1445 |
| 9,254,171 B2* | 2/2016 | Trees .................... | A61B 18/18 |
| 9,265,566 B2* | 2/2016 | O'Neill .............. | A61B 18/1445 |
| 9,265,570 B2* | 2/2016 | Heard ................ | A61B 18/1442 |
| 9,272,128 B2* | 3/2016 | Seddon ................. | A61M 39/12 |

FOREIGN PATENT DOCUMENTS

JP        4948955 B2      3/2012

OTHER PUBLICATIONS

Korean Office Action issued on Jul. 15, 2014, in counterpart Korean Application No. 10-2014-0001947 (3 pages, in Korean).

* cited by examiner

*Primary Examiner* — Max Hindenburg

(57) ABSTRACT

The present invention relates to a surgical grasper for measuring force, the surgical grasper having a first gripping part and a second gripping part, the first gripping part being provided with a first recess portion recessed inwardly from an outer surface of the first gripping part, the surgical grasper including: a first elastic dielectric body having one surface surface-contacting the first recess portion; an electrode part including a pair of electrodes opposed to each other on opposite surfaces of the first elastic dielectric body and having a distance between the electrodes, varied by external force applied thereto; and a first finishing part surface-contacting the other surface of the first elastic dielectric body and formed to correspond to the first recess portion to thereby be inserted into the first recess portion.

18 Claims, 7 Drawing Sheets

US 9,421,069 B2

SURGICAL GRASPER FOR MEASURING FORCE

CROSS-REFERENCE TO RELATED APPLICATION

This application claims the benefit of priority under 35 U.S.C. §119(a) of Korean Patent Application No. 10-2014-0001947, filed on Jan. 7, 2014, with the Korean Intellectual Property Office, the entire disclosure of which is incorporated herein by reference for all purposes.

FIELD

The present invention relates to a surgical grasper for measuring force and more particularly, to a surgical grasper for measuring force, capable of effectively gasping a tissue by maintaining a shape of the grasper, while facilitating the measurement of micro-force applied to the tissue.

BACKGROUND

Recently, a great quantity of researches on robots have been conducted and various types of robots have developed and are commercially being used. In particular, applications of surgical robots capable of performing an operation instead of a doctor's hands have greatly anticipated.

By using such a surgical robot, hand tremors may be removed and a region of a human body with which it may be infeasible for a human's hand to come into contact, the region being hidden by bones to be thereby invisible to the naked eyes, may be subjected to surgery, such that a surgery operation may be significantly, precisely performed.

However, currently commercialized surgical robots have merely provided image information on a body region to have surgery, but due to the absence of a tactile sensing member, it may be difficult to confirm information regarding force applied by the surgical robot to a tissue when a robot performs an operation, in particular, when the robot operates a tissue having a high level of damage possibility, whereby damage may be applied to the tissue.

Accordingly, researches into installing a device for precisely measuring force on an operation terminal or the like, of the surgical robot have been conducted, but in the case of the device for measuring force, it may be difficult to accurately measure force in all directions and further, it may be infeasible to mount a sensor on an arm of the robot as well as to maintain a shape of the robot arm.

SUMMARY

Therefore, an aspect of exemplary embodiments of the present invention may provide a surgical grasper for measuring force, capable of grasping a surgical object by maintaining a shape of the grasper, as well as effectively measuring force applied to the surgical object.

According to an embodiment of the present invention, there is provided a surgical grasper having a first gripping part and a second gripping part disposed to face each other while being movable in directions toward each other and apart from each other so as to grasp a surgical object, the first gripping part being provided with a first recess portion recessed inwardly from an outer surface of the first gripping part, the surgical grasper including: a first elastic dielectric body having one surface surface-contacting the first recess portion; an electrode part including a pair of electrodes opposed to each other on opposite surfaces of the first elastic dielectric body and having a distance between the electrodes, varied by external force applied thereto; and a first finishing part surface-contacting the other surface of the first elastic dielectric body and formed to correspond to the first recess portion to thereby be inserted into the first recess portion.

The second gripping part may be provided with a second recess portion recessed inwardly from a surface of the second gripping part facing the first grasping part, and the surgical grasper may further include a second elastic dielectric body having one surface surface-contacting the second recess portion; and a second finishing part surface-contacting the other surface of the second elastic dielectric body and formed to correspond to the second recess portion to be inserted into the second recess portion, the electrodes of the electrode part being disposed on opposite surfaces of the second elastic dielectric body so as to be opposed to each other.

The first recess portion may be formed in a longitudinal direction of the first gripping part, and the second recess portion may be formed in a lateral direction of the second gripping part.

An outer surface of the first recess portion and an outer surface of the second recess portion may be insulated from each other.

The first finishing part and the second finishing part may be insulated from each other.

The first recess portion and the second recess portion may have widths decreasing inwardly.

The first recess portion and the second recess portion may have both side surfaces symmetrical with regard to each other.

The first recess portion may be formed to have a conical shape or a polypyramid shape.

DETAILED DESCRIPTION

Figure 1:
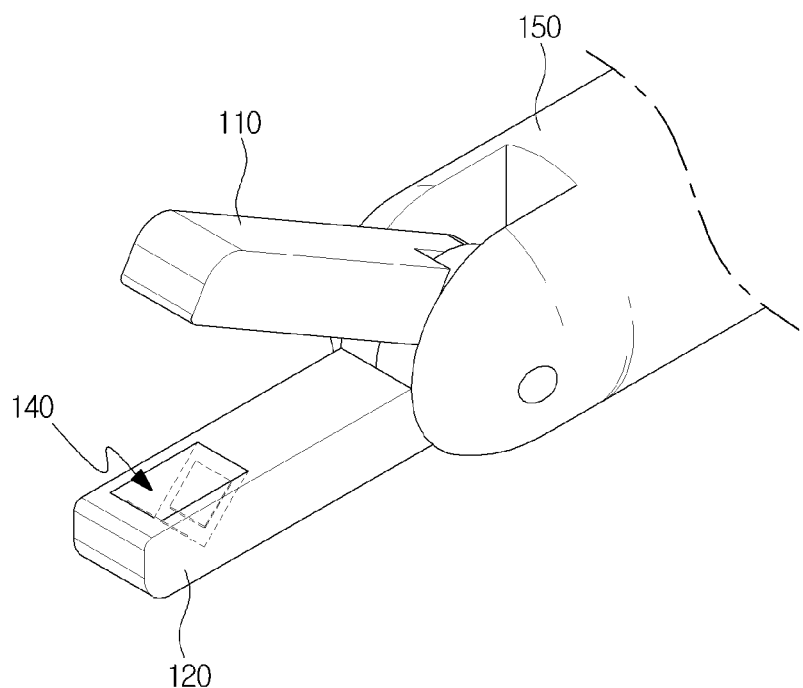
FIG. 1 is a schematic perspective view of a surgical grasper for measuring force according to an exemplary embodiment of the present invention.

Exemplary embodiments of the present disclosure will now be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

In the drawings, the shapes and dimensions of elements may be exaggerated for clarity, and the same reference numerals will be used throughout to designate the same or like elements.

Hereinafter, a surgical grasper 100 for measuring force according to an exemplary embodiment of the present invention will be described in detail with reference to the attached drawings.

Figure 2:
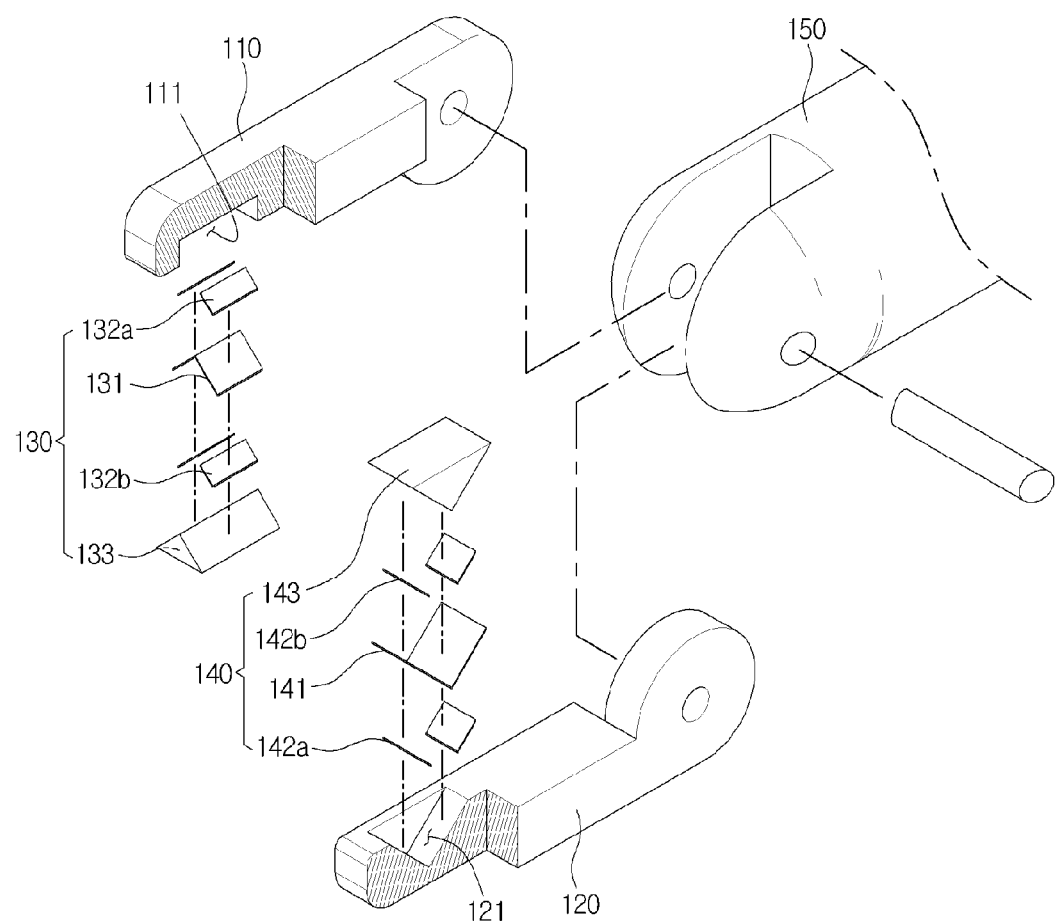
FIG. 2 is a schematic exploded view of the surgical grasper for measuring force illustrated in FIG. 1.

FIG. 1 is a schematic perspective view of a surgical grasper for measuring force according to an exemplary embodiment of the present invention. FIG. 2 is a schematic exploded view of the surgical grasper for measuring force illustrated in FIG. 1.

Referring to FIGS. 1 and 2, the surgical grasper 100 for measuring force according to an exemplary embodiment of the present invention may effectively grasp an object to have surgery (hereinafter, referred to as "a surgical object") by maintaining a shape of the grasper and may accurately measure force applied to the surgical object by mounting a sensor on a region contacting the surgical object. The surgical grasper 100 for measuring force according to an exemplary embodiment of the present invention may include a first gripping part 110, a second gripping part 120, a first sensing part 130, a second sensing part 140, and a body part 150.

The first gripping part 110 and the second gripping part 120, gripping the surgical object, may be members disposed to face each other while forming a predetermined angle therebetween, and movably provided in directions toward each other and apart from each other.

That is, the first gripping part 110 and the second gripping part 120 may move in directions toward each other until they come into contact with the surgical object to thereby grasp the surgical object, while moving in directions apart from each other to thereby allow the surgical object to be separated from a space between the first gripping part 110 and the second gripping part 120.

Meanwhile, a first recess portion 111 may be formed in an outer surface of the first gripping part 110 facing the surgical object, the first sensing part 130 being installed in the first recess portion 111, and a second recess portion 121 may be formed in an outer surface of the second gripping part 120 facing the surgical object, the second sensing part 140 being installed in the second recess portion 121.

Here, the first recess portion 111 and the second recess portion 121 may preferably be arranged to face each other.

In addition, the first recess portion 111 may be formed to have a shape corresponding to a first finishing part 133 of the first sensing part 130, and the second recess portion 121 may be formed to have a shape corresponding to a second finishing part 143 of the second sensing part 140.

FIG. 3 is a bottom view and a plan view schematically illustrating an outer surface of a first grasping part and an outer surface of a second grasping part in the surgical grasper for measuring force illustrated in FIG. 1.

Figure 3A:
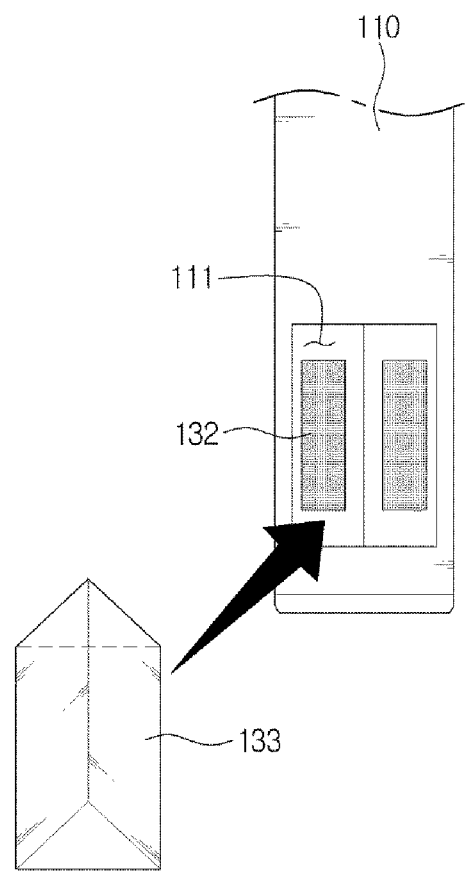
FIGS. 3A and 3B are a bottom view and a plan view schematically illustrating an outer surface of a first grasping part and an outer surface of a second grasping part in the surgical grasper for measuring force illustrated in FIG. 1.
Figure 3B:
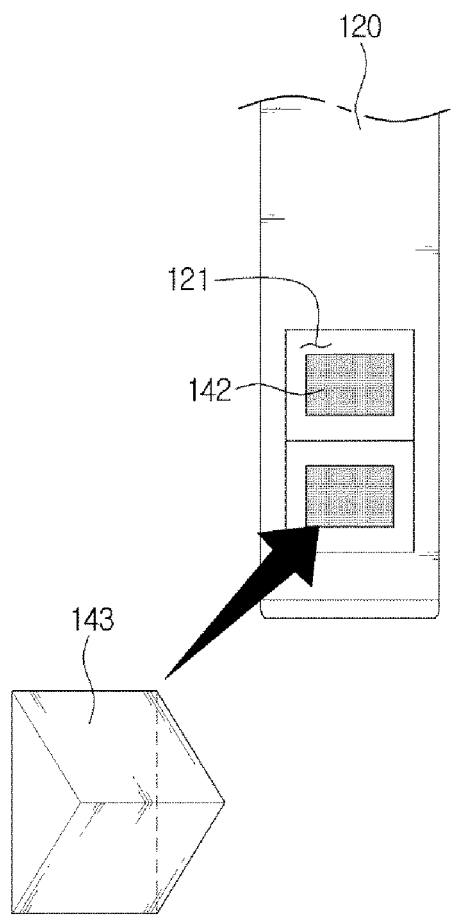

Referring to FIG. 3A, in an exemplary embodiment of the present invention, the first recess portion 111 may be formed in a longitudinal direction of the first gripping part 110, while having a width decreasing inwardly from the outer surface of the first gripping part 110. Referring to FIG. 3B, the second recess portion 121 may be formed in a lateral direction of the second gripping part 120, while having a width decreasing inwardly from the outer surface of the second gripping part 120.

That is, a direction of formation of the first recess portion 111 may intersect with a direction of formation of the second recess portion 121. The reason for this is to measure all of force exerted in 6-axis directions, which will be described later.

FIG. 4 is a bottom view and a plan view schematically illustrating an outer surface of a first grasping part and an outer surface of a second grasping part in a surgical grasper for measuring force according to a modified example modified from FIG. 1.

Figure 4A:
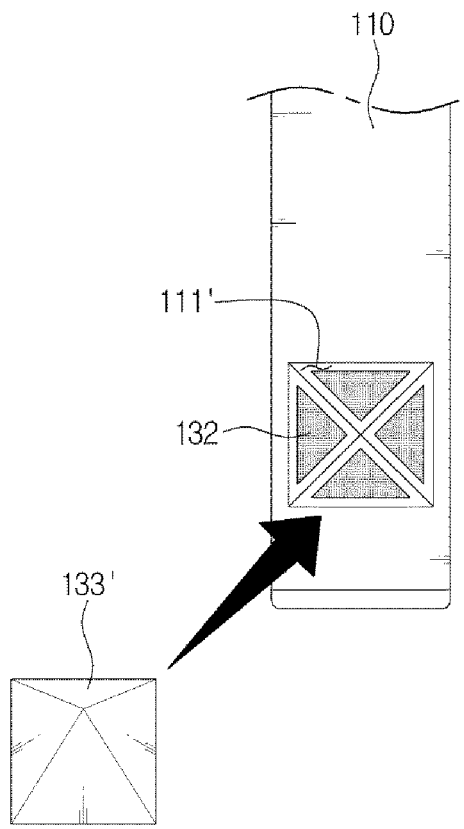
FIGS. 4A and 4B are a bottom view and a plan view schematically illustrating an outer surface of a first grasping part and an outer surface of a second grasping part in a surgical grasper for measuring force according to a modified example modified from FIG. 1.
Figure 4B:
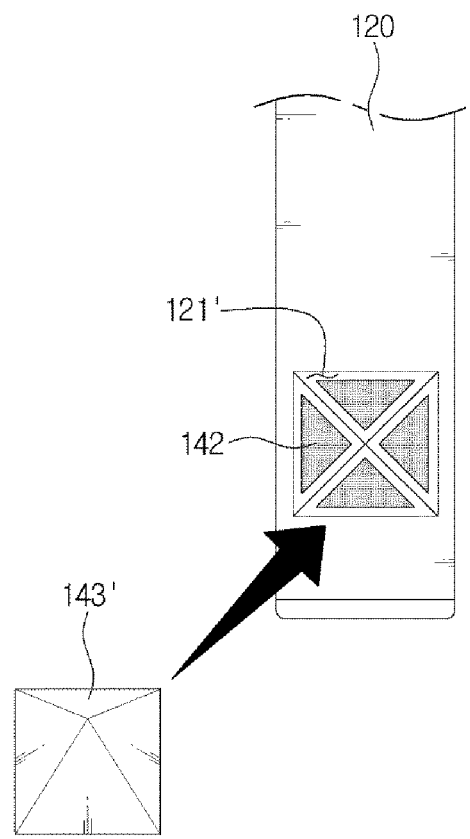

Referring to FIGS. 4A and 4B, a first recess portion 111' and a second recess portion 121' provided as modified examples of the first recess portion 111 and the second recess portion 121 may both have conical shapes or polypyramid shapes, such that all of force exerted in 6-axis directions may be measured.

Meanwhile, at least the outer surface of the first recess portion 111 and the outer surface of the second recess portion 121 may be electrically insulated from the first sensing part 130 or the second sensing part 140 to be described later. The outer surface of the first recess portion 111 and the outer surface of the second recess portion 121 may have an insulating layer formed thereon or may be grounded.

Meanwhile, an end portion of the first gripping part 110 and an end portion of the second gripping part 120 may be pivotally connected to each other.

The first sensing part 130 may be installed in the first recess portion 111 and may measure force applied to the surgical object by allowing the outer surface thereof to contact the surgical object. The first sensing part 130 may include a first elastic dielectric body 131, first electrode parts 132, and the first finishing part 133.

The first elastic dielectric body 131 may be a member inserted into the first recess portion 111 and having a surface surface-contacting the first recess portion 111.

In an exemplary embodiment of the present invention, the first elastic dielectric body 131 may be formed of a polydimethylsiloxane (PDMS) substance, but is not limited thereto.

The first electrode parts 132 may be a pair of electrodes disposed on opposite surfaces of the first elastic dielectric body 131 so as to be opposed to each other and having a distance therebetween, varying depending on external force exerted thereto.

In other words, the first electrode parts 132 may be disposed such that a pair of electrodes may be disposed to be spaced apart from each other by a distance equal to a thickness of the first elastic dielectric body 131, with the first elastic dielectric body 131 interposed therebetween. Here, the first elastic dielectric body 131 may be compressed at the time of applying external force thereto, such that the distance between the first electrode parts 132 may be varied.

The first finishing part 133 may be provided on an opposite surface of the first elastic dielectric body 131 opposite to the surface-contacting surface thereof, to finish the first recess portion 111. Here, an outer surface of the first finishing part 133 may partially protrude from the outer surface of the first gripping part 110.

In an exemplary embodiment of the present invention, the first finishing part 133 may be formed to correspond to the first recess portion 111 and may protrude from the outer surface of the first gripping part 110 by an amount equal to the thickness of the first elastic dielectric body 131, but is not limited thereto.

The second sensing part 140 may be inserted into the second recess portion 121 and may measure force applied to the surgical object by allowing the outer surface thereof to contact the surgical object. The second sensing part 140 may include a second elastic dielectric body 141, second electrode parts 142, and the second finishing part 143.

Here, since constitutions of the second elastic dielectric body 141, the second electrode parts 142, and the second finishing part 143 configuring the second sensing part 140 are substantially identical to those of the first elastic dielectric body 131, the first electrode parts 132, and the first finishing part 133 configuring the first sensing part 130, a detailed description thereof will be omitted.

Here, concrete coupling relationships between the first gripping part 110 and the first sensing part 130 and between the second gripping part 120 and the second sensing part 140 will be described. First, as for the coupling relationship between the first gripping part 110 and the first sensing part 130, the first recess portion 111 may be formed in the longitudinal direction of the first gripping part 110 and have a depth maximized in a central region thereof but reduced in directions away from the central region. That is, the first recess portion 111 may be recessed in a generally triangular prismatic shape.

That is, one first electrode part 132a of the first electrode parts 132 may be disposed on left and right side surfaces of the first recess portion 111, and the first elastic dielectric body 131 may be disposed on the first electrode part 132a.

Here, the other first electrode part 132b may be disposed on an upper surface of the first elastic dielectric body 131 in a position opposed to the first electrode part 132a.

In addition, the first finishing part 133 may be disposed on an upper portion of the other first electrode part 132b, and the first finishing part 133 may also have a triangular prismatic shape. Here, the first finishing part 133 may be movable by receiving external force from the upper portion of the other first electrode part 132b.

That is, the first finishing part 133 may be moved by external force applied thereto, whereby the distance between the first electrode parts 132 may be changed.

Here, a coupling relationship between the second recessed portion 121 and the second sensing part 140 is substantially identical to the coupling relationship between the first gripping part 110 and the first sensing part 130; however, since the second recessed portion 121 is formed in the lateral direction of the second gripping part 120, the coupling relationship between the second recessed portion 121 and the second sensing part 140 has a difference in that the second electrode parts 142 may be formed on front and rear surfaces of the second recessed portion 121.

Meanwhile, coupling relationships between the first gripping part 110 and the first sensing part 130 and between the second gripping part 120 and the second sensing part 140 according to a modified example modified from an exemplary embodiment of the present invention will be explained. The first recess portion 111 may be recessed in a polypyramid shape, in particular, a quadrangular pyramid shape. In this case, one first electrode part 132a of the first electrode parts 132 may be disposed on each of four side surfaces of the quadrangular pyramid and then, the first elastic dielectric body 131, the other first electrode part 132b, and the first finishing part 133 may be sequentially disposed on the first electrode part 132a.

Here, since the second recess portion 121 may be formed to have a quadrangular pyramid shape, the second sensing part 140 may be disposed in the same manner as that of the first sensing part 130.

The body part 150, a member coupling the end portion of the first gripping part 110 and the end portion of the second gripping part 120 that are pivotally connected to each other, may be used as an arm portion of a surgical robot, but is not limited thereto.

Hereinafter, operations of the surgical grasper 100 for measuring force according to an exemplary embodiment of the present invention will be described.

Before the description regarding operations of the surgical grasper, operational principles of the sensing parts 130 and 140 will be explained.

In the case that the above-described operational principles are expressed as a mathematical formula, it may be identical to the following Mathematical Formula 1.

$C_0 = (\epsilon_0 \cdot \epsilon_r \cdot A_0)/h_0$ ($C_0$: a capacitance value of a dielectric substance before deformation)

$C = C_0(1+S)^2$ ($C$: a capacitance value of a dielectric substance after deformation)   [Mathematical Formula 1]

Figure 6:
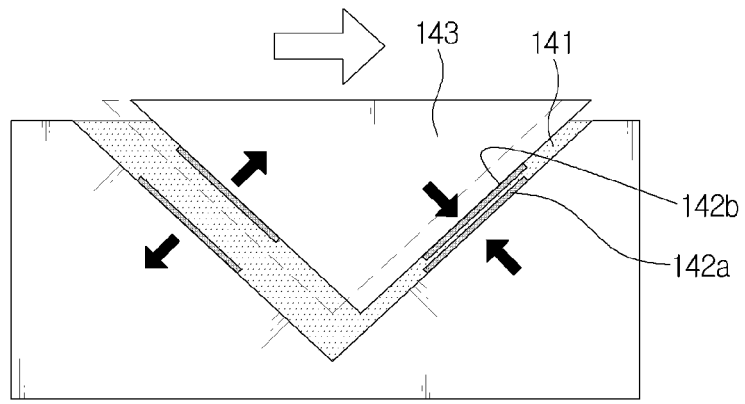
FIG. 6 is a cross-sectional view schematically illustrating a form in which shear force is applied to the sensing part of the surgical grasper for measuring force, illustrated in FIG. 1.

Here, a capacitance value before external force is applied is defined as $C_0$, a dielectric constant of a dielectric substance is defined as Er, a cross-sectional area of the electrode is defined as $A_0$, and a thickness of the dielectric substance is defined as $h_0$. Referring to FIG. 6, a capacitance value is defined as C, and strain is defined as S after the dielectric substance is deformed by applying external force thereto.

In addition, in the case that a dielectric constant in vacuum is defined as $\epsilon_0$ ($8.854 \times 10^{-12}$ F/m), variations in capacitance before and after external force is applied according to an exemplary embodiment of the present invention are expressed by the abovementioned Mathematical Formula 1.

In view of the abovementioned Mathematical Formula 1, in the case that capacitance levels are measured before and after external force is applied, the value of strain S may be calculated after external force is applied and using the value, a magnitude of external force may be confirmed.

On the basis of such operational principles, a method of measuring external force applied to the surgical object in the surgical grasper 100 for measuring force will be explained based on the second gripping part 120.

Figure 5:
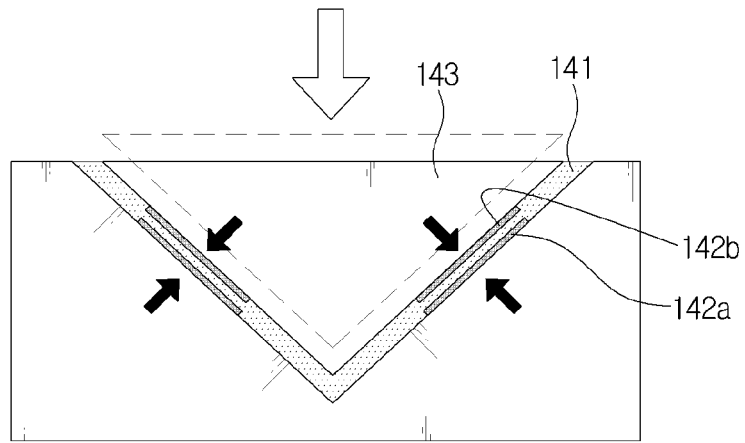
FIG. 5 is a cross-sectional view schematically illustrating a form in which normal force is applied to the sensing part of the surgical grasper for measuring force, illustrated in FIG. 1.

FIG. 5 is a cross-sectional view schematically illustrating a form in which normal force is applied to the sensing part of the surgical grasper for measuring force, illustrated in FIG. 1.

Referring to FIG. 5, in the case that normal force is applied onto the second finishing part 143, left and right side surfaces of the second elastic dielectric body 141 may be simultaneously compressed, and a level of capacitance of the second electrode parts 142 disposed on the left and right side surfaces of the second elastic dielectric body 141 may be increased. However, depending on a position to which external force is applied, a degree to which the left and right side surfaces of the second elastic dielectric body 141 are compressed may be different, and an increased amount of capacitance of the second electrode parts 142 disposed on the left and right side surfaces of the second elastic dielectric body 141 may be different.

FIG. 6 is a cross-sectional view schematically illustrating a form in which shear force is applied to the sensing part of the surgical grasper for measuring force, illustrated in FIG. 1.

Referring to FIG. 6, in the case that shear force is applied onto the second finishing part 143, the left side surface of the second elastic dielectric body 141 may be expanded and the right side surface thereof may be compressed. Thus, a level of capacitance of the second electrode parts 142 disposed on the left side surface of the second elastic dielectric body 141 may be decreased, while a level of capacitance of the second electrode parts 142 disposed on the right side surface of the second elastic dielectric body 141 may be increased.

Figure 7:
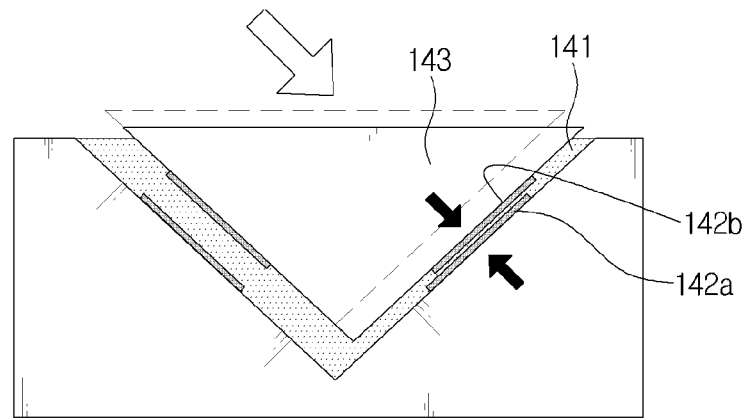
FIG. 7 is a cross-sectional view schematically illustrating a form in which normal force and shear force are simultaneously applied to the sensing part of the surgical grasper for measuring force, illustrated in FIG. 1.

FIG. 7 is a cross-sectional view schematically illustrating a form in which normal force and shear force are simultaneously applied to the sensing part of the surgical grasper for measuring force, illustrated in FIG. 1.

FIG. 7 illustrates a case in which normal force and shear force are simultaneously applied onto the second finishing part 143. In the case that force is applied in a right-downward direction, the left side surface of the second elastic dielectric body 141 may not be expanded or compressed, and a distance between the second electrode parts 142 may not be changed. Therefore, a level of capacitance of the second electrode parts 142 disposed on the left side surface of the second elastic dielectric body 141 may be uniform.

On the other hand, the right side surface of the second elastic dielectric body 141 may be compressed, and a level of capacitance of the second electrode parts 142 disposed on the right side surface of the second elastic dielectric body 141 may be increased.

Meanwhile, the aforementioned operational principles may be applied as is to the case of a surgical grasper for measuring force according to a modified example modified from an exemplary embodiment of the present invention. However, the modified example has a difference in that the number of portions in which variations in capacitance need to be measured is four, rather than two as in an exemplary embodiment of the present invention.

As set forth, according to exemplary embodiments of the present invention, a surgical grasper for measuring force, capable of effectively grasping a surgical object by maintaining a shape of the grasper, may be provided.

In addition, a sensing part may be mounted on a region contacting a tissue, whereby a magnitude of force applied to the tissue may be accurately measured.

While the present disclosure has been shown and described in connection with the embodiments, it will be apparent to those skilled in the art that modifications and variations can be made without departing from the spirit and scope of the disclosure as defined by the appended claims.

What is claimed is:

1. A surgical grasper, comprising;
   a first gripping part and a second gripping part facing the first gripping part, wherein the first gripping part and the second gripping part are movable toward each other and away from each other, and wherein the first gripping part comprises a first recess portion recessed inwardly from an outer surface of the first gripping part;
   a first elastic dielectric body having a first surface contacting the first recess portion;
   a first electrode part comprising a pair of electrodes opposed to each other on the first elastic dielectric body; and
   a first finishing part contacting a second surface of the first elastic dielectric body, corresponding in shape to the first recess portion, and configured to be inserted into the first recess portion,
   wherein the distance between the electrodes is determined based on a force applied to the first finishing part, and
   wherein the force is measured by using variations of capacitance of the first electrode part.

2. The surgical grasper according to claim 1, further comprising;
   a second elastic dielectric body having a first surface contacting a second recess portion;
   a second electrode part comprising a pair of electrodes opposed to each other on the second elastic dielectric body; and
   a second finishing part contacting a second surface of the second elastic dielectric body, corresponding in shape to the second recess portion, and configured to be inserted into the second recess portion,
   wherein the second gripping part comprises the second recess portion recessed inwardly from the second gripping part and facing the first grasping part,
   wherein the distance between the electrodes of the second electrode part is determined based on a force applied to the second finishing part, and
   wherein the force is measured by using variation of capacitance of the second electrode part.

3. The surgical grasper according to claim 2, wherein the first recess portion is formed in a longitudinal direction of the first gripping part, and
   the second recess portion is formed in a lateral direction of the second gripping part.

4. The surgical grasper according to claim 2, wherein an outer surface of the first recess portion and an outer surface of the second recess portion are insulated from each other.

5. The surgical grasper according to claim 2, wherein the first finishing part and the second finishing part are insulated from each other.

6. The surgical grasper according to claim 2, wherein the first recess portion and the second recess portion have widths decreasing inwardly.

7. The surgical grasper according to claim 6, wherein the first recess portion and the second recess portion comprise side surfaces symmetrical with regard to each other.

8. The surgical grasper according to claim 3, wherein the first recess portion and the second recess portion comprise widths decreasing inwardly.

9. The surgical grasper according to claim 8, wherein the first recess portion and the second recess portion comprise side surfaces symmetrical with regard to each other.

10. The surgical grasper according to claim 4, wherein the first recess portion and the second recess portion comprise widths decreasing inwardly.

11. The surgical grasper according to claim 10, wherein the first recess portion and the second recess portion comprises side surfaces symmetrical with regard to each other.

12. The surgical grasper according to claim 5, wherein the first recess portion and the second recess portion comprise widths decreasing inwardly.

13. The surgical grasper according to claim 12, wherein the first recess portion and the second recess portion comprise side surfaces symmetrical with regard to each other.

14. The surgical grasper according to claim 1, wherein the first recess portion comprises a conical shape or a polypyramid shape.

15. The surgical grasper according to claim 2, wherein the first recess portion comprises a conical shape or a polypyramid shape.

16. The surgical grasper according to claim 3, wherein the first recess portion comprises a conical shape or a polypyramid shape.

17. The surgical grasper according to claim 4, wherein the first recess portion comprises a conical shape or a polypyramid shape.

18. The surgical grasper according to claim 5, wherein the first recess portion comprises a conical shape or a polypyramid shape.

* * * * *